US009460496B2

(12) United States Patent
Ishihara

(10) Patent No.: US 9,460,496 B2
(45) Date of Patent: Oct. 4, 2016

(54) FLUORESCENCE OBSERVATION APPARATUS, FLUORESCENCE OBSERVATION SYSTEM, AND METHOD FOR FLUORESCENCE IMAGE PROCESSING

(71) Applicant: OLYMPUS CORPORATION, Tokyo (JP)

(72) Inventor: Yasushige Ishihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 256 days.

(21) Appl. No.: 14/100,422

(22) Filed: Dec. 9, 2013

(65) Prior Publication Data

US 2014/0098207 A1 Apr. 10, 2014

Related U.S. Application Data

(63) Continuation of application No. PCT/JP2011/064184, filed on Jun. 21, 2011.

(51) Int. Cl.
*A61B 1/04* (2006.01)
*G06T 5/00* (2006.01)
(Continued)

(52) U.S. Cl.
CPC ............ *G06T 5/006* (2013.01); *A61B 1/0005* (2013.01); *A61B 1/00059* (2013.01);
(Continued)

(58) Field of Classification Search
CPC ............ A61B 1/0005; A61B 1/00059; A61B 1/00186; A61B 1/043; A61B 1/05; A61B 1/0646; A61B 1/0669; G06T 5/006
USPC .......................................................... 348/68
See application file for complete search history.

(56) References Cited

U.S. PATENT DOCUMENTS 8,442,347 B2 *  5/2013  Sakagami ............ G02B 21/365
                                                                382/254
2001/0045506 A1 * 11/2001  Masuyama .......... G02B 21/368
                                                                250/201.3

(Continued)

FOREIGN PATENT DOCUMENTS

EP       1006386 A1    6/2000
JP       62-247232 A  10/1987
(Continued)

OTHER PUBLICATIONS

International Search Report dated Jul. 19, 2011 issued in PCT/JP2011/064184.
(Continued)

*Primary Examiner* — Shan Elahi
(74) *Attorney, Agent, or Firm* — Scully, Scott, Murphy & Presser, PC

(57) ABSTRACT

There is provided a fluorescence observation apparatus, including: a lighting section including a light source emitting illumination light and excitation light; a fluorescence imaging section picking up fluorescence generated on a subject and acquiring a fluorescence image; a returned light imaging section picking up returned light returned from the subject and acquiring a returned light image; a preprocessing section multiplying at least either the fluorescence image or the returned light image by a coefficient in which a distance property of fluorescence intensity and a distance property of returned light intensity, which are acquired in advance with respect to a standard sample, come to be in a relation directly proportional to each other and generating a fluorescence image for correction and a returned light image for correction; and a fluorescence image correction section dividing the fluorescence image for correction by the returned light image for correction.

11 Claims, 6 Drawing Sheets

(51) Int. Cl.
*A61B 1/00* (2006.01)
*A61B 1/05* (2006.01)
*A61B 1/06* (2006.01)

(52) U.S. Cl.
CPC .......... *A61B 1/00186* (2013.01); *A61B 1/043* (2013.01); *A61B 1/05* (2013.01); *A61B 1/0646* (2013.01); *A61B 1/0669* (2013.01)

(56) References Cited

U.S. PATENT DOCUMENTS

| | | | | |
|---|---|---|---|---|
| 2003/0016301 A1* | 1/2003 | Aizaki | ................ | H04N 5/2352 348/345 |
| 2004/0196457 A1* | 10/2004 | Aono | ................ | G01N 21/6458 356/318 |
| 2004/0196550 A1* | 10/2004 | Shimizu | ................ | G02B 21/06 359/388 |
| 2005/0002091 A1* | 1/2005 | Amano | ............. | G02B 21/0044 359/368 |
| 2006/0017913 A1* | 1/2006 | Kawamata | ............. | A61B 1/043 356/35.5 |
| 2008/0296511 A1* | 12/2008 | Kawamata | ............. | A61B 1/043 250/458.1 |
| 2009/0296203 A1* | 12/2009 | Kojima | ................ | G02B 21/365 359/363 |
| 2010/0103250 A1* | 4/2010 | Ishihara | ................... | A61B 1/05 348/61 |
| 2010/0245550 A1 | 9/2010 | Ishihara | | |
| 2010/0245551 A1 | 9/2010 | Morita | | |
| 2010/0245619 A1 | 9/2010 | Watanabe et al. | | |
| 2011/0001061 A1* | 1/2011 | Ishihara | ............ | A61B 1/00009 250/458.1 |
| 2011/0009702 A1* | 1/2011 | Morishita | .......... | A61B 1/00096 600/178 |
| 2011/0012025 A1* | 1/2011 | Takei | ................... | A61B 1/043 250/458.1 |
| 2011/0017923 A1* | 1/2011 | Kubo | ................ | A61B 1/00009 250/458.1 |
| 2011/0068278 A1* | 3/2011 | Morishita | ............. | A61B 1/043 250/458.1 |
| 2011/0121200 A1* | 5/2011 | Watanabe | ............. | A61B 1/043 250/458.1 |
| 2011/0267458 A1* | 11/2011 | Kubo | ................ | A61B 1/00009 348/135 |
| 2011/0267493 A1* | 11/2011 | Kubo | ................ | A61B 1/00009 348/223.1 |
| 2013/0113907 A1* | 5/2013 | Ono | ......................... | A61B 1/05 348/68 |
| 2013/0307952 A1* | 11/2013 | Ishihara | ................. | A61B 1/043 348/68 |
| 2014/0078279 A1* | 3/2014 | Shida | .................... | G06T 7/0083 348/68 |
| 2014/0184769 A1* | 7/2014 | Ishihara | ............. | A61B 1/00009 348/68 |
| 2014/0213871 A1* | 7/2014 | Watanabe | .......... | A61B 5/02042 600/371 |
| 2014/0301617 A1* | 10/2014 | Shida | ................ | A61B 1/00009 382/128 |

FOREIGN PATENT DOCUMENTS

| | | |
|---|---|---|
| JP | 3-58729 A | 9/1991 |
| JP | 2001-137173 A | 5/2001 |
| JP | 2003-111716 A | 4/2003 |
| JP | 2006-175052 A | 7/2006 |
| JP | 2008229025 A | 10/2008 |
| JP | 2010-220894 A | 10/2010 |
| WO | 2008008231 A2 | 1/2008 |
| WO | WO 2010110138 A1 | 9/2010 |

OTHER PUBLICATIONS

Extended Supplementary European Search Report dated Mar. 13, 2014 issued in corresponding Application No. / Patent No. 11868025.5-1660 PCT/JP2011064184.

* cited by examiner

FIG. 2

| OBSERVATION DISTANCE | 200 | ... | 120 | ... | 25 | ... | 10 |
|---|---|---|---|---|---|---|---|
| RETURNED LIGHT IMAGE | 331 | ... | 294 | ... | 4617 | ... | 14000 |
| FLUORESCENCE IMAGE | 5031 | ... | 5893 | ... | 53126 | ... | 27000 |
| RETURNED LIGHT GAIN | 1 | ... | 1 | ... | 1 | ... | 1 |
| FLUORESCENCE GAIN | 150 | ... | 150 | ... | 100 | ... | 30 |
| RETURNED LIGHT EXPOSURE TIME | 20 | ... | 15 | ... | 10 | ... | 7 |
| FLUORESCENCE EXPOSURE TIME | 100 | ... | 100 | ... | 70 | ... | 30 |
| NORMALIZED RETURNED LIGHT IMAGE | 16.6 | ... | 37.5 | ... | 461.7 | ... | 2000 |
| NORMALIZED FLUORESCENCE IMAGE | 33.5 | ... | 72.2 | ... | 758.9 | ... | 3000 |
| FLUORESCENCE/RETURNED LIGHT | 2.024 | ... | 1.923 | ... | 1.644 | ... | 1.500 |

FIG. 3

| NORMALIZED RETURNED LIGHT IMAGE | 16.6 | ... | 37.5 | ... | 461.7 | ... | 2000 |
|---|---|---|---|---|---|---|---|
| COEFFICIENT | 2.024 | ... | 1.923 | ... | 1.644 | ... | 1.500 |

FLUORESCENCE OBSERVATION APPARATUS, FLUORESCENCE OBSERVATION SYSTEM, AND METHOD FOR FLUORESCENCE IMAGE PROCESSING

CROSS REFERENCE TO RELATED APPLICATIONS

This is a continuation of International Application PCT/JP2011/064184, with an international filing date of Jun. 21, 2011, which is hereby incorporated by reference herein in its entirety. The contents of Japanese Patent Application No. 2010-119750 are incorporated herein by reference.

TECHNICAL FIELD

The present invention relates to a fluorescence observation apparatus, a fluorescence observation system, and a method for fluorescence image processing.

BACKGROUND ART

There has conventionally been known a method for correcting brightness variations in fluorescence images caused by observation distances and angles by dividing a fluorescence image by a reflected light image (see, for example, PTL 1 to PTL 3).

CITATION LIST

Patent Literature

{PTL 1}
Japanese Unexamined Patent Application, Publication No. Sho 62-247232
{PTL 2}
Japanese Examined Patent Application, Publication No. Hei 3-58729
{PTL 3}
Japanese Unexamined Patent Application, Publication No. 2006-175052

SUMMARY OF INVENTION

Technical Problem

Since fluorescence and reflected light are different in dependency of brightness to be captured on an observation distance and in dependency of brightness to be captured on an observation angle, simply dividing the fluorescence image by the reflected light image is not sufficient for correcting influence of the distance and the angle.

Solution to Problem

In a first aspect of the present invention, there is provided a fluorescence observation apparatus, including: a lighting section adapted to include a light source that emits illumination light and excitation light; a fluorescence imaging section adapted to pick up fluorescence generated on a subject and to acquire a fluorescence image; a returned light imaging section adapted to pick up returned light returned from the subject and to acquire a returned light image; a preprocessing section adapted to multiply at least either the fluorescence image or the returned light image by a coefficient in which a distance property of fluorescence intensity and a distance property of returned light intensity, which are acquired in advance with respect to a standard sample, come to be in a relation directly proportional to each other and to generate a fluorescence image for correction and a returned light image for correction; and a fluorescence image correction section adapted to divide the fluorescence image for correction, which was generated by the preprocessing section, by the returned light image for correction.

In a second aspect of the present invention, there is provided a fluorescence observation apparatus, including: a lighting section adapted to include a light source that emits illumination light and excitation light; a fluorescence imaging section adapted to pick up fluorescence generated on a subject and to acquire a fluorescence image; a returned light imaging section adapted to pick up returned light returned from the subject and to acquire a returned light image; a preprocessing section adapted to multiply at least either the fluorescence image or the returned light image by a coefficient in which an angle property of fluorescence intensity and an angle property of returned light intensity, which are acquired in advance with respect to a standard sample, come to be in a relation directly proportional to each other and to generate a fluorescence image for correction and a returned light image for correction; and a fluorescence image correction section adapted to divide the fluorescence image for correction, which was generated by the preprocessing section, by the returned light image for correction.

In a third aspect of the present invention, there is provided a fluorescence observation system, including: the above-described fluorescence observation apparatus; and a calibration device adapted to be connected to the fluorescence observation apparatus and to calculate the coefficient, wherein the calibration device includes a standard sample and an observation distance setting mechanism that changeably sets an observation distance of the fluorescence observation apparatus with respect to the standard sample, and based on the observation distance set by the observation distance setting mechanism as well as a fluorescence image and a returned light image acquired by photographing the standard sample with the fluorescence observation apparatus, a coefficient that causes a distance property of fluorescence intensity and a distance property of returned light intensity to be directly proportional when at least either the fluorescence image or the returned light image is multiplied thereby is calculated and is stored in the storage section.

In a fourth aspect of the present invention, there is provided a fluorescence observation system, including: the above-described fluorescence observation apparatus; and a calibration device adapted to be connected to the fluorescence observation apparatus and to calculate the coefficient, wherein the calibration device includes a standard sample and an observation angle setting mechanism that changeably sets an observation angle of the fluorescence observation apparatus with respect to the standard sample, and based on the observation angle set by the observation angle setting mechanism as well as a fluorescence image and a returned light image acquired by photographing the standard sample with the fluorescence observation apparatus, a coefficient that causes an angle property of fluorescence intensity and an angle property of returned light intensity to be directly proportional when at least either the fluorescence image or the returned light image is multiplied thereby is calculated and is stored in the storage section.

Advantageous Effects of Invention

According to the present invention, the effects of being able to sufficiently remove dependency on distance and the like that remain in an image subjected to dividing operation and to perform observation with fluorescence images that are high in quantitatively are demonstrated.

BRIEF DESCRIPTION OF DRAWINGS

FIG. 2 is a table view showing an example of association between a gradation value, gain, and exposure time of images and normalized images for deriving a coefficient for use in the fluorescence observation apparatus of FIG. 1, and a coefficient derived therefrom.

FIG. 3 is a table view showing an example of association between a gradation value of a normalized returned light image and a coefficient derived from FIG. 2.

DESCRIPTION OF EMBODIMENTS

Hereinafter, a description is given of a fluorescence observation apparatus 1 and a method for fluorescence image processing according to one embodiment of the present invention with reference to the drawings.

Figure 1:
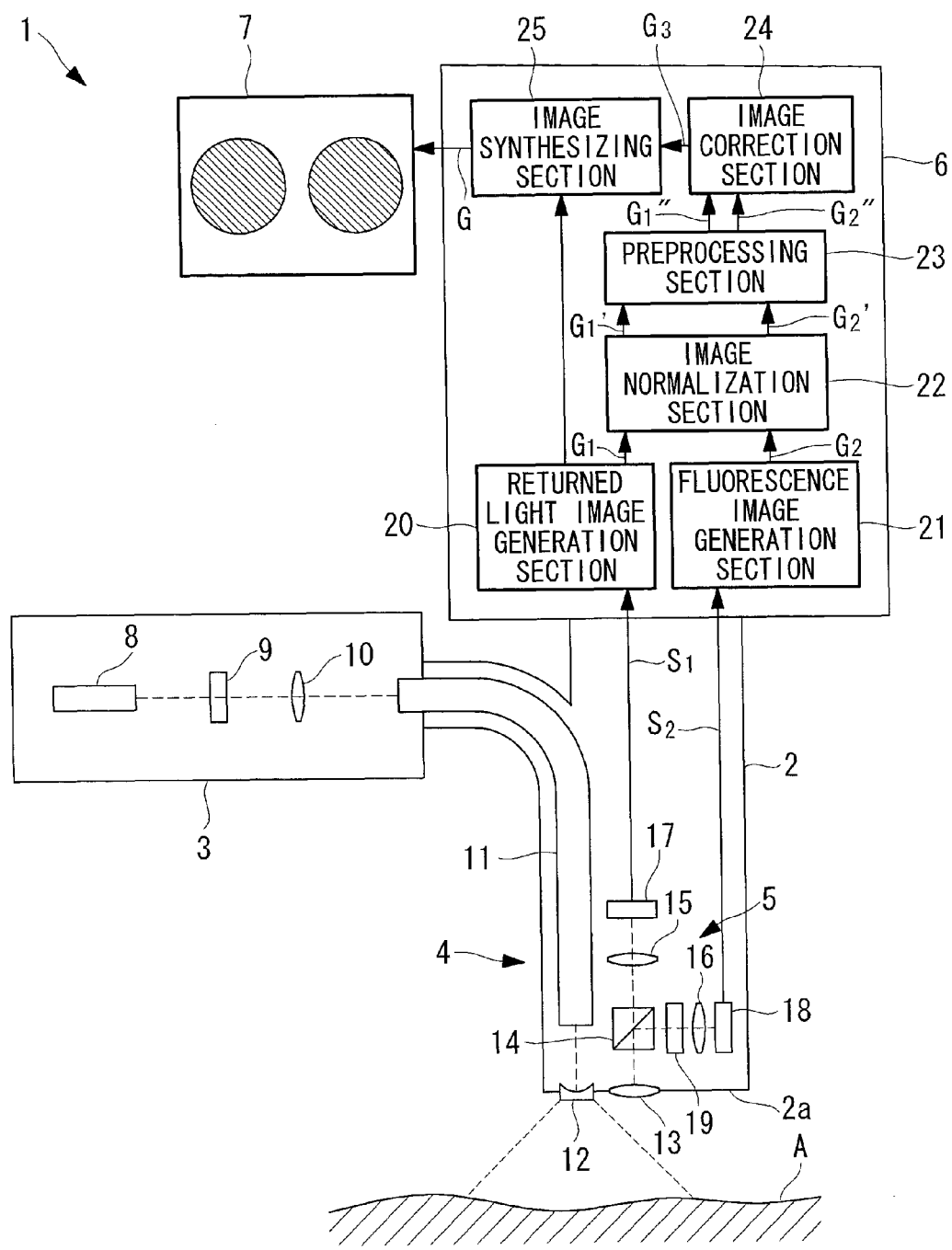
FIG. 1 is an overall structure view showing a fluorescence observation apparatus according to one embodiment of the present invention.

The fluorescence observation apparatus 1 according to the present embodiment is an endoscopic device including, as shown in FIG. 1, an elongated insertion section 2 to be inserted into a body, a light source (lighting section) 3, a lighting unit (lighting section) 4 that emits illumination light and excitation light that come from the light source 3, from the top end of the insertion section 2 to an observation target A, an imaging unit 5 provided at the top end of the insertion section 2 to acquire image information of a body tissue that is the observation target A, an image processing section 6 placed at a base end side of the insertion section 2 to process the image information acquired by the imaging unit 5, and a monitor 7 which displays images G processed by the image processing section 6.

The light source 3 includes a xenon lamp 8, a filter 9 that cuts out excitation light and illumination light (for example, in the wavelength band of 400 to 740 nm) from the illumination light emitted from the xenon lamp 8, and a coupling lens 10 that collects the excitation light and the illumination light cut out by the filter 9.

The lighting unit 4 includes a light guide fiber 11 placed along generally the overall length of a longitudinal direction of the insertion section 2 to guide the excitation light and the illumination light collected by the coupling lens 10, and an illumination optical system 12 provided at a top end of the insertion section 2 to diffuse the excitation light and the illumination light guided by the light guide fiber 11 and to emit the light to the observation target A that faces a front end surface 2a of the insertion section 2.

The imaging unit 5 includes an objective lens 13 that collects returned light returned from a specified observation area of the observation target A, a dichroic mirror (diverging section) 14 that reflects the light (excitation light and fluorescence) having an excitation wavelength or longer among the returned light collected by the objective lens 13, while transmitting illumination light having a wavelength shorter than the excitation wavelength, two condensing lenses (imaging optical systems) 15 and 16 that respectively collect the illumination light that transmitted the dichroic mirror 14 and the fluorescence reflected by the dichroic mirror 14, and two image sensors 17 and 18 like a CCD which image the fluorescence and the illumination light collected by the condensing lenses 15 and 16. In the drawing, reference numeral 19 designates an excitation light cutoff filter that blocks the excitation light from the light reflected by the dichroic mirror 14 (which, for example, transmits only the light in the wavelength band of 760 to 850 nm).

The image processing section 6 includes a returned light image generation section 20 that generates a returned light image $G_1$ based on returned light image information $S_1$ acquired by the image sensor 17, a fluorescence image generation section 21 that generates a fluorescence image $G_2$ based on fluorescence image information $S_2$ acquired by the image sensor 18, and an image normalization section 22 that normalizes the returned light image $G_1$ and the fluorescence image $G_2$ generated by these returned light image generation section 20 and fluorescence image generation section 21 and generates a normalized returned light image $G_1'$ and a normalized fluorescence image $G_2'$.

The image processing section 6 also includes a preprocessing section 23 that generates a returned light image for correction $G_1''$ and a fluorescence image for correction $G_2''$ from the normalized returned light image $G_1'$ and the normalized fluorescence image $G_2'$ generated by the image normalization section 22, an image correction section 24 that performs image correction by dividing the fluorescence image for correction $G_2''$ generated by the preprocessing section 23 by the returned light image for correction $G_1''$, and an image synthesizing section 25 that synthesizes a corrected fluorescence image $G_3$ generated in the image correction section 24 and the returned light image $G_1$ generated in the returned light image generation section 20 to generate an image G.

The image synthesizing section 25 is adapted to synthesize the image G so that, for example, the returned light image $G_1$ and the corrected fluorescence image $G_3$ are placed in parallel and simultaneously displayed on the monitor 7.

Here, the fluorescence image $G_2$ may be, for example, a fluorescence image from a fluorescent dye Cy7. Particularly, if a tumor-specific fluorescent agent, such as a fluorescent agent prepared by combining an antibody for a cancer-specific molecule CEA (Anti-CEA antibody) and Cy7, is given in advance to the observation target A, then the tumor-specific fluorescence image $G_2$ can be obtained. Furthermore, as the returned light image $G_1$, an image based on returned light that is formed from illumination light reflected on the surface of the observation target A and returned light that is formed by diffusion inside the observation target A may be used for example.

The image normalization section 22 is adapted to normalize the returned light image $G_1$ and the fluorescence image $G_2$ with use of a relational expression shown in Formula 1.

$$\text{Normalized gradation value} = \frac{\text{Acquired image gradation value}}{\text{Exposure time}} \times \frac{\text{Specified gain}}{\text{Observation gain}} \quad \text{(Formula 1)}$$

More specifically, assuming that the returned light image $G_1$ and the fluorescence image $G_2$ of 16-bit gradation are acquired by the image sensors 17 and 18, exposure time and gain are adjusted so that a gradation value of each pixel falls within this range, and therefore normalization is performed to have generalized observation conditions. For example, in Formula 1, the specified gain is set to 1 at the time of white light observation and set to 100 at the time of fluorescence observation.

The preprocessing section 23 includes a storage section (illustration omitted) that stores a coefficient, which causes a distance property of fluorescence intensity with respect to a standard sample and a distance property of returned light intensity with respect to the same standard sample to be directly proportional to each other, in association with the returned light intensity. For each pixel of a returned light image that has been inputted, a coefficient associated with a gradation value of each pixel is read from the storage section and is multiplied so as to generate a returned light image for correction $G_1''$. In this case, in the preprocessing section 23, an inputted fluorescence image $G_2$ is outputted without any change as a fluorescence image for correction $G_2''$.

Here, FIGS. 2 and 3 show coefficient examples calculated based on the gradation values of the returned light image $G_1$ and the fluorescence image $G_2$ when the observation distance is changed in the range of, for example, 10 to 200 mm and a phantom or an organ of a pig and the like is observed as a standard sample.

More specifically, when the gradation value (returned light intensity) of one pixel in the returned light image $G_1$ that has been acquired is 16.6, the gradation value of the pixel is multiplied by a coefficient of 2.024. By repeating this procedure for all the pixels, the returned light image for correction $G_1''$ is obtained. When the gradation value of any one of the pixels is a value between two gradation values shown in FIG. 3, a coefficient obtained by linear interpolation of two coefficients corresponding to the gradation values of FIG. 2 is multiplied.

In order to perform fluorescence observation of the observation target A with use of the thus-configured fluorescence observation apparatus 1 according to the present embodiment, the top end 2a of the insertion section 2 is placed so as to face the observation target A, and the lighting unit 4 is operated to emit illumination light and excitation light that come from the light source 3, from the illumination optical system 12 at the top end 2a of the insertion section 2 toward the observation target A through the light guide fiber 11. Returned light that reflects on the surface of the observation target A and returns therefrom is collected by the objective lens 13, and is transmitted through the dichroic mirror 14 before being picked up by the image sensor 17. In contrast, fluorescence generated inside the observation target A upon emission of excitation light is collected by the objective lens 13 and is reflected by the dichroic mirror 14, before being picked up by the image sensor 18.

When returned light image information $S_1$ acquired by the image sensor 17 is inputted into the returned light image generation section 20, a returned light image $G_1$ is generated, and when fluorescence image information $S_2$ acquired by the image sensor 18 is inputted into the fluorescence image generation section 21, a fluorescence image $G_2$ is generated. The returned light image $G_1$ and the fluorescence image $G_2$, which have been generated, are inputted into the image normalization section 22, and are normalized by Formula 1 into a normalized returned light image $G_1'$ and a normalized fluorescence image $G_2'$, which are converted into a returned light image for correction $G_1''$ and a fluorescence image for correction $G_2''$ in the preprocessing section 23 (preprocessing step).

In the present embodiment, the normalized returned light image $G_1'$ is multiplied by the coefficient to be a returned light image for correction $G_1''$, while the normalized fluorescence image $G_2'$ becomes a fluorescence image for correction $G_2''$ as-is.

Then, in the image correction section 24, the fluorescence image for correction $G_2''$ is divided by the returned light image for correction $G_1''$, as a result of which a corrected fluorescence image $G_3$ is acquired (fluorescence image correction step), and the corrected fluorescence image $G_3$ is synthesized with the returned light image $G_1$ in the image synthesizing section 25 and is displayed on the monitor 7.

The coefficient to be multiplied by the normalized returned light image $G_1'$ in the preprocessing section 23 is a ratio of the normalized fluorescence image $G_2'$ and the normalized returned light image $G_1'$ that were acquired with use of a standard sample. The coefficient is selected so that the distance property of fluorescence intensity of the normalized fluorescence image $G_2'$ in the standard sample matches the distance property of returned light intensity of the normalized returned light image $G_1'$ also in the standard sample. Therefore, in the image correction section 24, the fluorescence image for correction $G_2''$ is divided by the returned light image for correction $G_1''$ that was obtained by multiplying the coefficient by the normalized returned light image $G_1'$ of the observation target A, so that a corrected fluorescence image $G_3$ having observation distance dependency being sufficiently reduced can be obtained. In other words, fluorescence observation high in quantitativity can advantageously be implemented.

Note that in the present embodiment, the fluorescence image $G_2$ and the returned light image $G_1$ acquired by the image sensors 18 and 17 include a noise attributed to dark current of the image sensors 18 and 17 and read operation. Furthermore, if the returned light image $G_1$ includes a pixel of which brightness value is zero at the time of performing a dividing process, a divided result becomes infinite and proper correction is hindered.

Accordingly, in the preprocessing section 23, an offset that removes a noise component, which is attributed to the dark current or read operation, may be given to the fluorescence image $G_2$, while an offset that removes a noise component, which is attributed to the dark current or read operation and which prevents the brightness value of all the pixels from becoming zero, may be given to the returned light image $G_1$.

Moreover, the returned light image $G_1$ may be an image obtained by observing not only surface reflection light and returned diffusion light from the observation target A, but also autofluorescence generated from the observation target A and fluorescence from other fluorescent agents that have fluorescent properties in the wavelength band different from that of the fluorescent agent used for acquisition of the fluorescence image $G_2$.

Furthermore, the image displayed arranged with the corrected fluorescence image $G_3$ on the monitor 7 may be a white reflected image separately acquired in place of the returned light image $G_1$.

Figure 4:
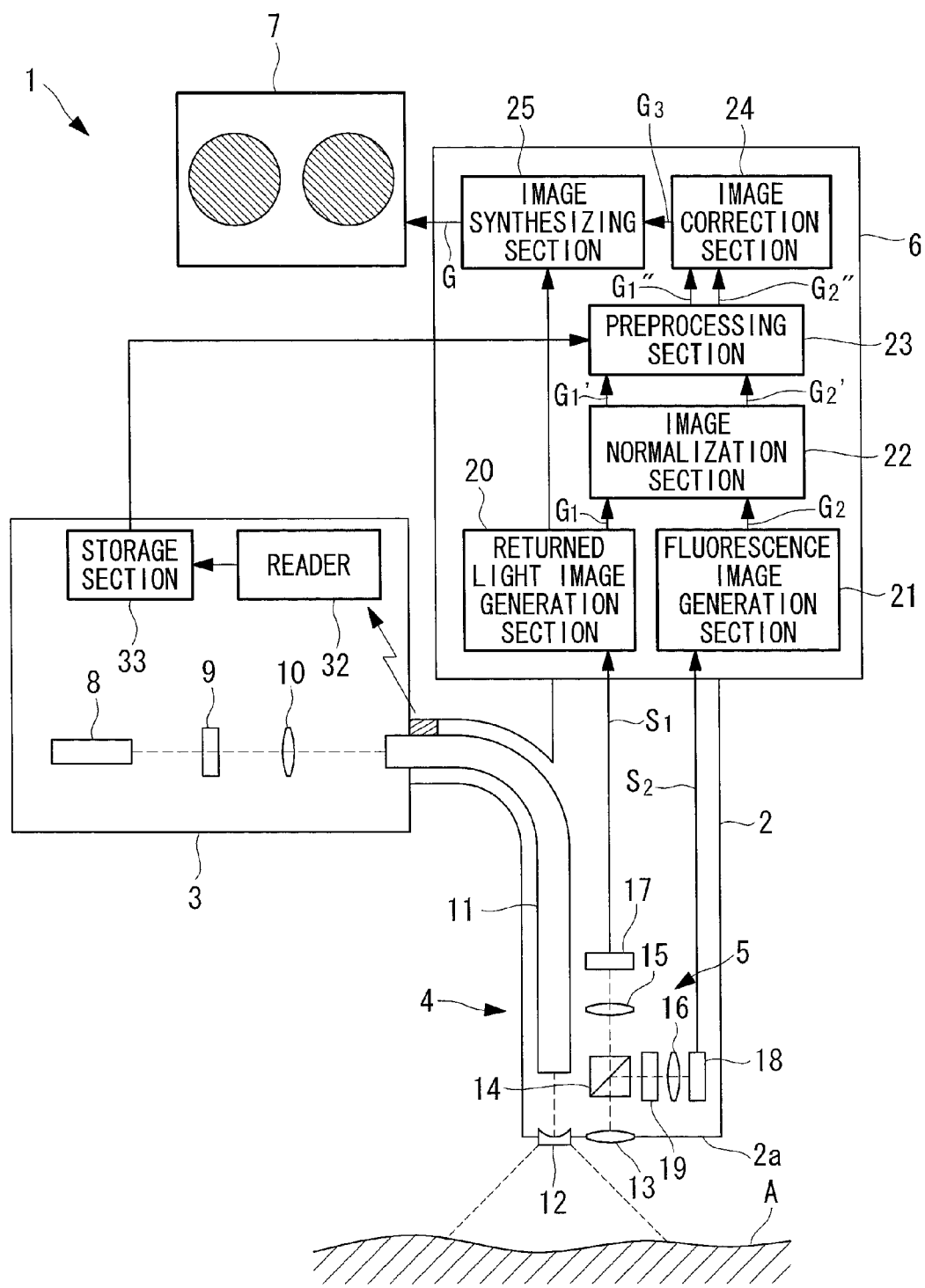
FIG. 4 is an overall structure view showing a modified example of the fluorescence observation apparatus of FIG. 1.

Moreover, in the present embodiment, the insertion section (attaching/detaching part) 2 may detachably be provided on the light source 3 as shown in FIG. 4. In this case, the insertion section 2 is detached and replaced with another insertion section 2, so that various optical systems included in the insertion section 2, such as the objective lens 13, are replaced. As a consequence, the coefficient is changed due to change in the numerical aperture (NA), the pupil diameter and the like of the objective lens 13, or due to change in the wavelength of fluorescence to be detected, the observation target area (stomach tissue, large intestine tissue, etc.) and the like.

Therefore, it is preferable that the insertion section 2 includes an IC chip 31 that stores identification information, while the light source 3 side to which the insertion section 2 is attached includes a reader 32 that reads the identification information inside the IC chip 31 and a storage section 33 that stores the identification information and coefficients suitable for respective insertion sections 2 in association with each other. The preprocessing section 23 may receive a coefficient corresponding to the identification information of an insertion section 2 outputted from the storage section 33, and may perform the above operation with the coefficient.

In this way, even when the insertion section 2 to be attached to the light source 3 is replaced, an optimal coefficient is set for the insertion section 2, and thereby the fluorescence image $G_3$ that is high in quantitativity can advantageously be acquired on a constant basis.

Furthermore, although the coefficient that matches the distance property of the returned light intensity with respect to a standard sample with the distance property of fluorescence intensity was employed in the present embodiment, the coefficient is not limited thereto but a coefficient that causes both the properties to be directly proportional may also be used.

Furthermore, a coefficient that is multiplied by the normalized fluorescence image $G_2'$ may be stored in place of the coefficient that is multiplied by the normalized returned light image $G_1'$, or the coefficients that are respectively multiplied by the normalized returned light image $G_1'$ and the normalized fluorescence image $G_2'$ may also be stored.

In the present embodiment, further, the configuration for reducing the observation distance dependency and performing fluorescence observation high in quantitativity was employed. However, the configuration for reducing the observation angle dependency may be employed instead. More specifically, in the preprocessing section 23, a ratio between the normalized fluorescence image $G_2'$ and the normalized returned light image $G_1'$ is multiplied by the normalized returned light image $G_1'$ of the observation target A, the images being are acquired with use of the standard sample with the observation angle being changed, i.e., a coefficient selected so that the angle property of fluorescence intensity of the normalized fluorescence image $G_2'$ in a standard sample is directly proportional to the angle property of returned light intensity of the normalized returned light image $G_1'$ in the standard sample. Then, in the image correction section 24, a fluorescence image for correction $G_2''$ is divided by the acquired returned light image for correction $G_1''$, so that a corrected fluorescence image $G_3$ having observation angle dependency being sufficiently reduced can be obtained. In other words, fluorescence observation high in quantitativity can advantageously be implemented.

A description is now given of a fluorescence observation system 40 according to one embodiment of the present invention with reference to the drawings.

Note that in the description of the present embodiment, component members identical in configuration to the fluorescence observation apparatus 1 according to the foregoing one embodiment are designated by identical reference numerals to omit the description thereof.

Figure 5:
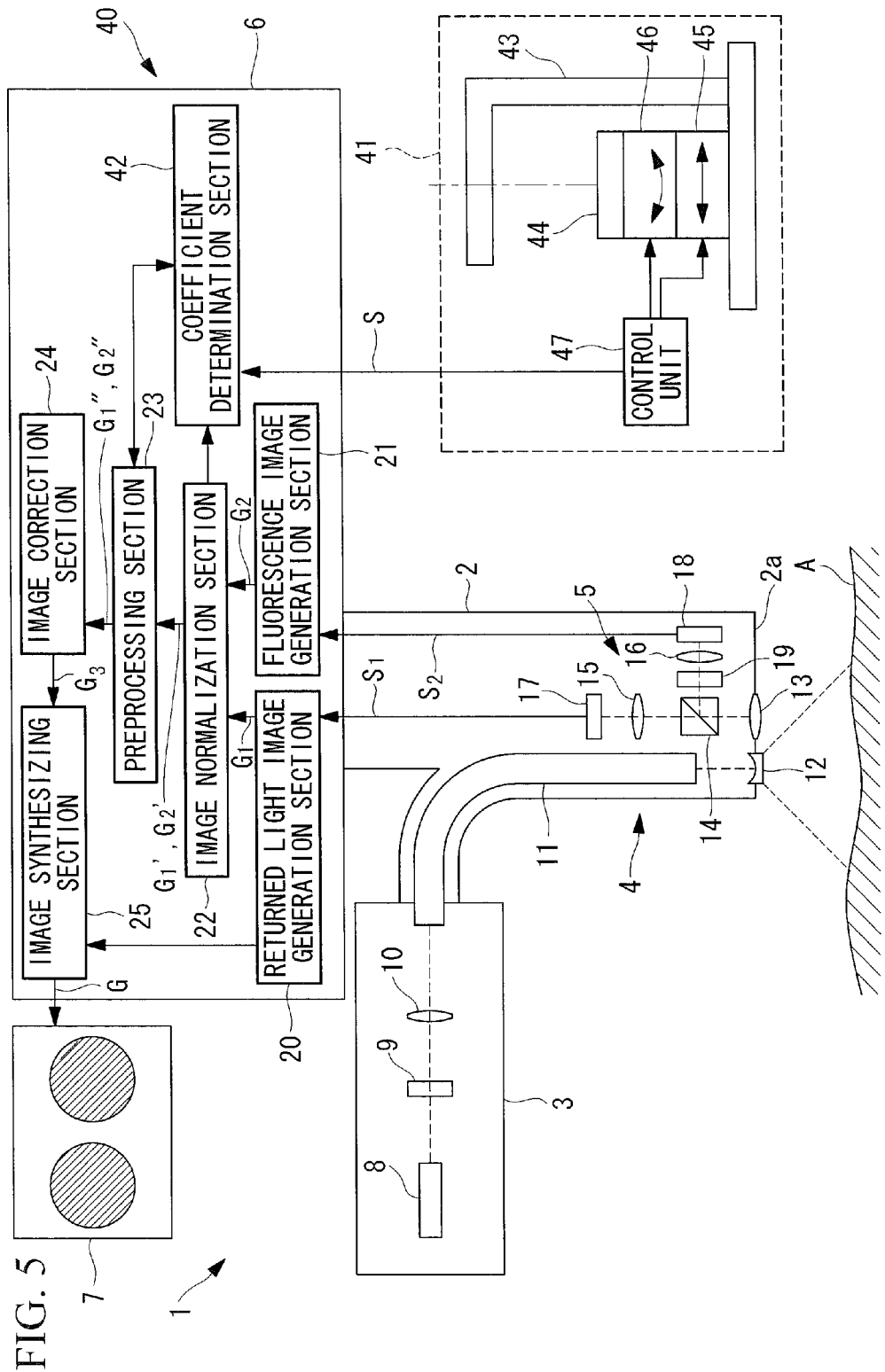
FIG. 5 is an overall structure view showing a fluorescence observation system according to one embodiment of the present invention.

As shown in FIG. 5, the fluorescence observation system 40 according to the present embodiment includes a fluorescence observation apparatus 1, and a calibration device 41 with the fluorescence observation apparatus 1 mounted thereon.

In the present embodiment, the fluorescence observation apparatus 1 includes a coefficient determination section 42 that calculates coefficients.

Figure 6:
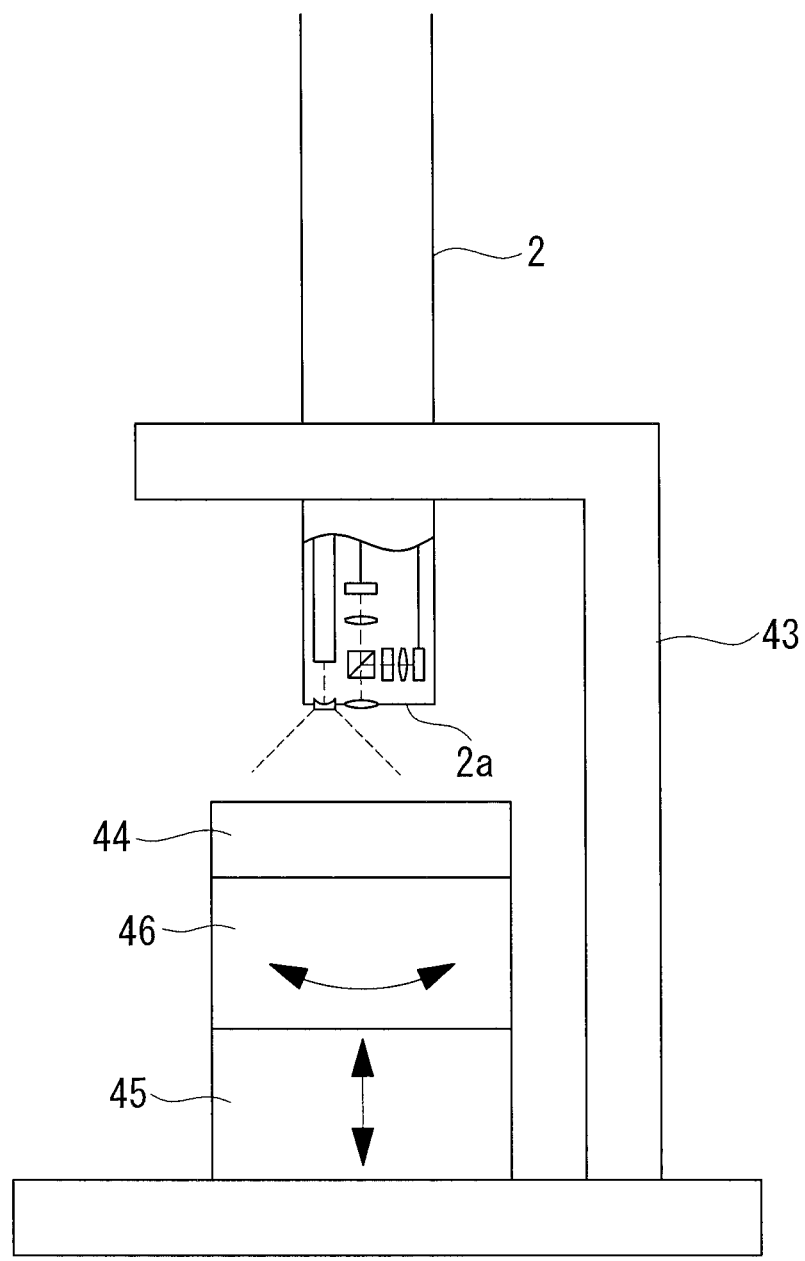
FIG. 6 is a view showing a calibration device in the fluorescence observation system of FIG. 1.

The calibration device 41 includes, as shown in FIGS. 5 and 6, a holder 43 that fixes the insertion section 2, a standard sample 44 that is made to face, with an observation distance, the front end surface 2a of the insertion section 2 fixed to the holder 43, a direct acting stage 45 that changes the observation distance between the front end surface 2a of the insertion section 2 and the standard sample 44, a tilt stage 46 that changes an angle (observation angle) of the surface of the standard sample 44 with respect to an optical axis of the objective lens 13, and a control unit 47 that controls these stages 45 and 46.

The control unit 47 is adapted to drive the stages 45 and 46 so as to change the observation distance or observation angle and to output a trigger signal S with a preset timing.

Moreover, the coefficient determination section 42 is adapted to receive the normalized fluorescence image $G_2'$ and the normalized returned light image $G_1'$ which are sent from the image normalization section 22, as well as to retain a brightness value of the normalized fluorescence image $G_2'$ and a brightness value of the normalized returned light image $G_1'$ at the time of receiving the trigger signal S from the control unit 47, to divide the brightness value of the normalized fluorescence image $G_2'$ by the brightness value of the normalized returned light image $G_1'$ so as to calculate a coefficient, and to store the calculated coefficient in association with the brightness value of the normalized returned light image $G_1'$.

To acquire coefficients with the observation distance being changed, the control unit 47 first drives the direct acting stage 45 so that the front end surface 2a of the insertion section 2 has an observation start distance with respect to the surface of the standard sample 44 as shown in FIG. 6. Next, after illumination light and excitation light are emitted from the unit 4 to the standard sample 44 to prepare the state of picking up returned light and fluorescence, the control unit 47 moves the stage 45 by a predetermined distance at a time, and outputs the trigger signal S every time the predetermined distance is moved. As a consequence, a plurality of coefficients acquired with a plurality of different observation distances are stored in association with the brightness values of the normalized returned light image $G_1'$ in the coefficient determination section 42.

In contrast, to acquire coefficients with the observation angle being changed, the control unit 47 first drives the direct acting stage 45 and the tilt stage 46 so that the front end surface 2a of the insertion section 2 has an observation start distance and angle with respect to the surface of the standard sample 44, as shown in FIG. 6. Next, after illumination light and excitation light are emitted from the unit 4 to the standard sample 44 to prepare the state of picking up returned light and fluorescence, the control unit 47 moves the tilt stage 46 by a predetermined distance at a time, and outputs the trigger signal S every time the predetermined distance is moved. As a consequence, a plurality of coefficients acquired at a plurality of different observation angles are stored in association with the brightness values of the normalized returned light image $G_1'$ in the coefficient determination section 42.

The coefficients with the observation distance being changed, and the coefficients with the observation angle being changed may properly be selected in accordance with observation conditions.

Moreover, the coefficient determination section 42 is adapted to calculate, upon input of a brightness value of the normalized returned light image $G_1'$ from the preprocessing section 23, a coefficient corresponding to the brightness value and to output the coefficient to the preprocessing section 23. More specifically, a plurality of coefficients associated with a plurality of brightness values of the normalized returned light images $G_1'$ prepared at intervals are stored in the coefficient determination section 42, and therefore when a brightness value in between these stored values is inputted, a new coefficient is calculated by interpolating the coefficient with the brightness values on both sides of the inputted brightness value, and is outputted to the preprocessing section 23.

Thus, according to the fluorescence observation system 40 in the present embodiment, every time the observation target A and the observation conditions, such as an optical system and a fluorescence wavelength for use in observation, are changed, the coefficient can be set in response to the changes, so that observation with a fluorescence image $G_3$ that is high in quantitativity can advantageously be implemented even with various observation targets A and under various observation conditions.

For example, when the fluorescence observation apparatus 1 is applied as an endoscope, it becomes possible to set optimal coefficients corresponding to different apparatus types, such as a rigid endoscope and an elasticity endoscope, or corresponding to different observation sites as in the case of an upper digestive endoscope and a lower digestive endoscope. Moreover, in the case of the fluorescence observation apparatus 1 of the same type, it is possible to set coefficients for individual apparatuses, irrespective of individual difference.

Note that as the standard sample 44 in the present embodiment, a phantom having the same diffusion or absorption characteristics as a living body to be observed may be used, or an excised tissue of a human or an animal (such as a pig and a mouse) may be used.

The following aspects of the invention are derived from the above embodiments.

In a first aspect of the present invention, there is provided a fluorescence observation apparatus, including: a lighting section adapted to include a light source that emits illumination light and excitation light; a fluorescence imaging section adapted to pick up fluorescence generated on a subject and to acquire a fluorescence image; a returned light imaging section adapted to pick up returned light returned from the subject and to acquire a returned light image; a preprocessing section adapted to multiply at least either the fluorescence image or the returned light image by a coefficient in which a distance property of fluorescence intensity and a distance property of returned light intensity, which are acquired in advance with respect to a standard sample, come to be in a relation directly proportional to each other and to generate a fluorescence image for correction and a returned light image for correction; and a fluorescence image correction section adapted to divide the fluorescence image for correction, which was generated by the preprocessing section, by the returned light image for correction.

According to the first aspect of the present invention, when excitation light is emitted from the lighting section to the subject, a fluorescent material which is present inside the subject is excited and fluorescence is generated thereby. The generated fluorescence is picked up by the fluorescence imaging section and a fluorescence image is acquired. Contrary to this, when illumination light is emitted from the lighting section to the subject, returned light, which is returned due to such action as being reflected on the surface of the subject, is picked up by the returned light imaging section and a returned light image is acquired. The acquired fluorescence image is corrected with use of the returned light image in the fluorescence image correction section.

In this case, prior to correction performed in the fluorescence image correction section, the preprocessing section multiplies at least either the fluorescence image or the returned light image by a coefficient in which a distance property of fluorescence intensity and a distance property of returned light intensity, which are acquired in advance with respect to a standard sample, come to be in a relation directly proportional to each other, so that a fluorescence image for correction and a returned light image for correction are generated.

More specifically, the fluorescence intensity of respective pixels that constitute a fluorescence image and the returned light intensity of respective pixels that constitute a returned light image are changed depending on distances from the lighting section to respective positions on the subject that correspond to the pixels, and the intensities can be approximated to exponential functions of the respective distances. Since exponents in the distance property of fluorescence intensity are different from exponents in the distance property of the returned light intensity, it is impossible to remove the distance dependency by simply dividing the fluorescence image by the returned light image. Therefore, the fluorescence intensity and the returned light intensity are respectively exponentiated in advance with reciprocals of the respective exponents in the distance properties, so that the distance property of fluorescence intensity and the distance property of returned light intensity come to be in a relation directly proportional to each other, and the distance dependency can be removed at the time of dividing operation.

Accordingly, based on the distance property of fluorescence intensity and the distance property of returned light intensity that are acquired in advance with respect to a standard sample, a coefficient that can provide, when at least either the fluorescence image or the returned light image is multiplied thereby, the same effect as the aforementioned exponentiation of the reciprocals of exponents is obtained in advance. The thus-obtained coefficient is multiplied by at least either the fluorescence image or the returned light image so as to generate a fluorescence image for correction and a returned light image for correction, and the fluorescence image for correction is divided by the returned light image for correction in the fluorescence image correction section. As a result, it becomes possible to provide a fluorescence image corrected so as to sufficiently reduce the distance dependency.

More specifically, according to the first aspect of the present invention, reduction in distance dependency can be achieved with higher precision than reduction through exponent approximation, so that fluorescence observation high in quantitativity can be implemented.

In a second aspect of the present invention, there is provided a fluorescence observation apparatus, including: a lighting section adapted to include a light source that emits illumination light and excitation light; a fluorescence imaging section adapted to pick up fluorescence generated on a subject and to acquire a fluorescence image; a returned light imaging section adapted to pick up returned light returned from the subject and to acquire a returned light image; a preprocessing section adapted to multiply at least either the fluorescence image or the returned light image by a coefficient in which an angle property of fluorescence intensity and an angle property of returned light intensity, which are acquired in advance with respect to a standard sample, come to be in a relation directly proportional to each other and to generate a fluorescence image for correction and a returned light image for correction; and a fluorescence image correction section adapted to divide the fluorescence image for correction, which was generated by the preprocessing section, by the returned light image for correction.

According to the second aspect of the present invention, prior to correction performed in the fluorescence image correction section, the preprocessing section multiplies at least either the fluorescence image or the returned light image by a coefficient in which an angle property of fluorescence intensity and an angle property of returned light intensity, which are acquired in advance with respect to a standard sample, come to be in a relation directly proportional to each other, so that a fluorescence image for correction and a returned light image for correction are generated.

More specifically, the fluorescence intensity of respective pixels that constitute a fluorescence image and the returned light intensity of respective pixels that constitute a returned light image are changed depending on angles from the lighting section to respective positions on the subject that correspond to the pixels, and the intensities can be approximated to exponential functions of the respective angles. Since exponents in the angle property of fluorescence intensity are different from exponents in the angle property of the returned light intensity, it is impossible to remove the angle dependency by simply dividing the fluorescence image by the returned light image. Therefore, the fluorescence intensity and the returned light intensity are respectively exponentiated in advance with reciprocals of the respective exponents in the angle properties, so that the angle property of fluorescence intensity and the angle property of returned light intensity come to be in a relation directly proportional to each other, and the angle dependency can be removed at the time of dividing operation.

Accordingly, based on the angle property of fluorescence intensity and the angle property of returned light intensity that are acquired in advance with respect to a standard sample, a coefficient that can provide, when at least either the fluorescence image or the returned light image is multiplied thereby, the same effect as the aforementioned exponentiation of the reciprocals of exponents is obtained in advance. The thus-obtained coefficient is multiplied by at least either the fluorescence image or the returned light image so as to generate a fluorescence image for correction and a returned light image for correction, and the fluorescence image for correction is divided by the returned light image for correction in the fluorescence image correction section. As a result, it becomes possible to provide a fluorescence image corrected so as to sufficiently reduce the angle dependency.

More specifically, according to the second aspect of the present invention, reduction in angle dependency can be achieved with higher precision than reduction through exponent approximation, so that fluorescence observation high in quantitativity can be implemented.

In the first aspect or the second aspect of the present invention, a storage section adapted to store the coefficient may be included, wherein the preprocessing section may multiply the coefficient stored in the storage section by at least either the fluorescence image or the returned light image.

With this configuration, simply performing multiplication by the coefficient stored in the storage section makes it possible to easily reduce the distance or angle dependency and to thereby implement fluorescence observation high in quantitativity.

Furthermore, according to the configuration, there may be included an attaching/detaching part adapted to be attached/detached in order to change observation conditions, the attaching/detaching part having identification information recorded thereon; and a reader adapted to read the identification information stored in the attaching/detaching part, wherein the storage section may store the identification information and the coefficient in association with each other.

With this configuration, when the attaching/detaching part is attached/detached and an observation condition is changed, the identification information stored in the attaching/detaching part is read by the reader, and the coefficient stored in the storage section in association with the identification information can be set. Examples of the attaching/detaching part include scopes in endoscopic devices, and examples of the observation conditions changed in relation to attachment/detachment include a numerical aperture (NA) and a pupil diameter of an objective optical system, a wavelength of observable fluorescence, and an observation target area (such as stomach and large intestine). As a consequence, an optimal coefficient can be set in accordance with the observation conditions. Even when the observation conditions are changed, fluorescence observation high in quantitativity can be implemented.

Further, in the first aspect or the second aspect of the present invention, the preprocessing section may normalize fluorescence intensity of each pixel in the fluorescence image and returned light intensity of each pixel in the returned light image with gain and exposure time in the fluorescence imaging section and the returned light imaging section, and may generate a normalized fluorescence image and a normalized returned light image. The preprocessing section may multiply at least either the normalized fluorescence image or the normalized returned light image by the coefficient to generate a fluorescence image for correction and a returned light image for correction.

With this configuration, even when different gain adjustment and exposure time adjustment are performed in the fluorescence imaging section and the returned light imaging section at the time of taking a fluorescence image and a returned light image, a normalized fluorescence image and a normalized returned light image having normalized gain and exposure time are generated, and with use of these normalized images, a fluorescence image for correction and a returned light image for correction are generated so that fluorescence observation with higher quantitativity can be implemented In a third aspect of the present invention, there is provided a fluorescence observation system, including: the above-described fluorescence observation apparatus; and a calibration device adapted to be connected to the fluorescence observation apparatus and to calculate the coefficient, wherein the calibration device includes a standard sample and an observation distance setting mechanism that changeably sets an observation distance of the fluorescence observation apparatus with respect to the standard sample, and based on the observation distance set by the observation distance setting mechanism as well as a fluorescence image and a returned light image acquired by photographing the standard sample with the fluorescence observation apparatus, a coefficient that causes a distance property of fluorescence intensity and a distance property of returned light intensity to be directly proportional when at least either the fluorescence image or the returned light image is multiplied thereby is calculated and is stored in the storage section.

According to the third aspect of the present invention, the standard sample is photographed with the fluorescence observation apparatus while the observation distance of the fluorescence observation apparatus with respect to the standard sample is changed with the observation distance setting mechanism of the calibration device, so that a distance property of fluorescence brightness and a distance property of returned light intensity of the standard sample can be obtained, and based on these distance properties, a coefficient that causes both the distance properties to be directly proportional can be calculated. Furthermore, the calculated coefficient is stored in the storage section of the fluorescence observation apparatus, so that at the time of fluorescence observation of the subject with the fluorescence observation apparatus, the coefficient calculated with precision can be used to perform fluorescence observation with higher quantitativity, irrespective of individual difference present among the fluorescence observation apparatuses and irrespective of individual difference among attaching/detaching parts, if present.

In a fourth aspect of the present invention, there is provided a fluorescence observation system, including: the above-described fluorescence observation apparatus; and a calibration device adapted to be connected to the fluorescence observation apparatus and to calculate the coefficient, wherein the calibration device includes a standard sample and an observation angle setting mechanism that changeably sets an observation angle of the fluorescence observation apparatus with respect to the standard sample, and based on the observation angle set by the observation angle setting mechanism as well as a fluorescence image and a returned light image acquired by photographing the standard sample with the fluorescence observation apparatus, a coefficient that causes an angle property of fluorescence intensity and an angle property of returned light intensity to be directly proportional when at least either the fluorescence image or the returned light image is multiplied thereby is calculated and is stored in the storage section.

According to the fourth aspect of the present invention, the standard sample is photographed with the fluorescence observation apparatus while the observation angle of the fluorescence observation apparatus with respect to the standard sample is changed with the observation angle setting mechanism of the calibration device, so that an angle property of fluorescence brightness and an angle property of returned light intensity of the standard sample can be obtained, and based on these angle properties, a coefficient that causes both the angle properties to be directly proportional can be calculated. Furthermore, the calculated coefficient is stored in the storage section of the fluorescence observation apparatus, so that at the time of fluorescence observation of the subject with the fluorescence observation apparatus, the coefficient calculated with precision can be used to perform fluorescence observation with higher quantitativity, irrespective of individual difference present among the fluorescence observation apparatuses and irrespective of individual difference among attaching/detaching parts, if present.

Moreover, in a fifth aspect of the present invention, there is provided a method for fluorescence image processing, including: a preprocessing step of, by using a fluorescence image acquired by picking up fluorescence generated on a subject upon emission of excitation light to the subject and a returned light image acquired by picking up returned light returned from the subject upon emission of illumination light to the subject, multiplying at least either the fluorescence image or the returned light image by a coefficient in which a distance property of fluorescence intensity and a distance property of returned light intensity, which are acquired in advance with respect to a standard sample, come to be in a relation directly proportional to each other and to generate a fluorescence image for correction and a returned light image for correction; and a fluorescence image correction step of dividing the fluorescence image for correction, which was generated in the preprocessing step, by the returned light image for correction.

REFERENCE SIGNS LIST

A Observation target (subject)
1 Fluorescence observation apparatus
2 Insertion section (attaching/detaching part)
3 Light source
4 Lighting unit (lighting section)
17 Image sensor (returned light imaging section)
18 Image sensor (fluorescence imaging section)
24 Image correction section
32 Reader (identification information reading means)
33 Storage section
40 Fluorescence observation system
41 Calibration device
42 Coefficient determination section
44 Standard sample
45 Direct acting stage (observation distance setting mechanism)
46 Tilt stage (observation angle setting mechanism)

The invention claimed is:
1. A fluorescence observation apparatus comprising:
a light source configured to emit illumination light and excitation light;
a fluorescence sensor configured to detect fluorescence generated by a specimen due to irradiation by the excitation light and to output fluorescence image information;
a returned light sensor configured to detect returned light from the specimen due to irradiation by the illumination light and to output returned light image information; and
a processor comprising hardware, wherein the processor is configured to:
 generate a fluorescence image based on the fluorescence image information;
 generate a returned light image based on the returned light image information;
 perform one of:
  a first process of:
   multiplying a gradation value of the fluorescence image by a coefficient to generate a fluorescence image for correction; and
   multiplying a gradation value of the returned light image by the coefficient to generate a returned light image for correction;
  a second process of:
   multiplying the gradation value of the fluorescence image by the coefficient to generate the fluorescence image for correction; and outputting the returned light image as the returned light image for correction; or
a third process of:
multiplying the gradation value of the returned light image by the coefficient to generate the returned light image for correction; and
outputting the fluorescence image as the fluorescence image for correction; and
divide the fluorescence image for correction by the returned light image for correction,
wherein the coefficient is calculated so that a first distance property and a second distance property come to be in relation directly proportional to each other,
wherein the first distance property is a distance property between a gradation value and an observation distance of a fluorescence image acquired in advance with respect to a standard sample, and
wherein the second distance property is a distance property between a gradation value and an observation distance of a returned light acquired in advance with respect to the standard sample.

2. The fluorescence observation apparatus according to claim 1, wherein the processor is configured to retrieve the coefficient from a storage.

3. The fluorescence observation apparatus according to claim 2, further comprising:
an attaching/detaching structure configured to be detachably attached to the light source;
an optical system, arranged to the attaching/detaching structure, configured to change observation conditions of the specimen;
an identification storage, arranged to the attaching/detaching structure, having identification information of the optical system stored thereon; and
a reader device configured to read the identification information stored in the identification storage,
wherein the storage is configured to store the identification information and the coefficient in association with each other.

4. A fluorescence observation system, comprising:
the fluorescence observation apparatus according to claim 2; and
a calibration device comprising:
an observation distance setting actuator configured to changeably set an observation distance of the fluorescence observation apparatus with respect to the standard sample,
wherein the processor is configured to:
calculate the coefficient based on the observation distance set by the observation distance setting actuator as well as a fluorescence image and a returned light image acquired by photographing the standard sample with the fluorescence observation apparatus; and
store the coefficient in the storage.

5. A fluorescence observation system, comprising:
the fluorescence observation apparatus according to claim 2; and
a calibration device comprising:
an observation angle setting actuator configured to changeably set an observation angle of the fluorescence observation apparatus with respect to the standard sample,
wherein the processor is configured to:
calculate the coefficient based on the observation angle set by the observation angle setting actuator as well as a fluorescence image and a returned light image acquired by photographing the standard sample with the fluorescence observation apparatus; and
store the coefficient in the storage.

6. The fluorescence observation apparatus according to claim 1,
wherein the processor is configured to:
normalize fluorescence intensity of each pixel in the fluorescence image and returned light intensity of each pixel in the returned light image with gain and exposure time in the fluorescence sensor and the returned light sensor to generate a normalized fluorescence image and a normalized returned light image; and
perform one of:
multiplying the normalized fluorescence image by the coefficient to generate the fluorescence image for correction, and multiplying the normalized returned light image by the coefficient to generate the returned light image for correction;
multiplying the normalized fluorescence image by the coefficient to generate the fluorescence image for correction, and outputting the normalized returned light image as the returned light image for correction; or
multiplying the normalized returned light image by the coefficient to generate the returned light image for correction, and outputting the normalized fluorescence image as the fluorescence image for correction.

7. A fluorescence observation apparatus comprising:
a light source configured to emit illumination light and excitation light;
a fluorescence sensor configured to detect fluorescence generated by a specimen due to irradiation by the excitation light and to output fluorescence image information;
a returned light sensor configured to detect returned light from the specimen due to irradiation by the illumination light and to output returned light image information; and
a processor comprising hardware, wherein the processor is configured to:
generate a fluorescence image based on the fluorescence image information;
generate a returned light image based on the returned light image information;
perform one of:
a first process of:
multiplying a gradation value of the fluorescence image by a coefficient to generate a fluorescence image for correction; and
multiplying a gradation value of the returned light image by the coefficient to generate a returned light image for correction;
a second process of:
multiplying the gradation value of the fluorescence image by the coefficient to generate the fluorescence image for correction; and
outputting the returned light image as the returned light image for correction; or
a third process of:
multiplying the gradation value of the returned light image by the coefficient to generate the returned light image for correction; and
outputting the fluorescence image as the fluorescence image for correction; and divide the fluorescence image for correction by the returned light image for correction,
wherein the coefficient is calculated so that a first angle property and a second angle property come to be in relation directly proportional to each other,
wherein the first angle property is an angle property between a gradation value and an observation angle of a fluorescence image acquired in advance with respect to a standard sample, and
wherein the second angle property is an angle property between a gradation value and an observation angle of a returned light acquired in advance with respect to the standard sample.

8. The fluorescence observation apparatus according to claim 7, wherein the processor is configured to retrieve the coefficient from a storage.

9. The fluorescence observation apparatus according to claim 8, further comprising:
an attaching/detaching structure configured to be detachably attached to the light source;
an optical system, arranged to the attaching/detaching structure, configured to change observation conditions of the specimen;
an identification storage, arranged to the attaching/detaching structure, having identification information of the optical system stored thereon; and
a reader device configured to read the identification information stored in the identification storage,
wherein the storage is configured to store the identification information and the coefficient in association with each other.

10. The fluorescence observation apparatus according to claim 7,
wherein the processor is configured to:
normalize fluorescence intensity of each pixel in the fluorescence image and returned light intensity of each pixel in the returned light image with gain and exposure time in the fluorescence sensor and the returned light sensor to generate a normalized fluorescence image and a normalized returned light image; and
perform one of:
multiplying the normalized fluorescence image by the coefficient to generate the fluorescence image for correction, and multiplying the normalized returned light image by the coefficient to generate the returned light image for correction;
multiplying the normalized fluorescence image by the coefficient to generate the fluorescence image for correction, and outputting the normalized returned light image as the returned light image for correction; or
multiplying the normalized returned light image by the coefficient to generate the returned light image for correction, and outputting the normalized fluorescence image as the fluorescence image for correction.

11. A method for processing:
a fluorescence image generated from fluorescence image information output by a fluorescence sensor configured to detect fluorescence generated by a specimen due to irradiation by excitation light; and
a returned light image generated from returned light image information output by a returned light sensor configured to detect returned light from the specimen due to irradiation by illumination light,
the method comprising:
performing one of:
a first process of:
multiplying, by a processor comprising hardware, a gradation value of the fluorescence image by a coefficient to generate a fluorescence image for correction; and
multiplying, by the processor, a gradation value of the returned light image by the coefficient to generate a returned light image for correction;
a second process of:
multiplying, by the processor, the gradation value of the fluorescence image by the coefficient to generate the fluorescence image for correction; and
outputting, by the processor, the returned light image as the returned light image for correction; or
a third process of:
multiplying, by the processor, the gradation value of the returned light image by the coefficient to generate the returned light image for correction; and
outputting, by the processor, the fluorescence image as the fluorescence image for correction; and
dividing, by the processor, the fluorescence image for correction by the returned light image for correct,
wherein the coefficient is calculated so that a first distance property and a second distance property come to be in relation directly proportional to each other,
wherein the first distance property is a distance property between a gradation value and an observation distance of a fluorescence image acquired in advance with respect to a standard sample, and
wherein the second distance property is a distance property between a gradation value and an observation distance of a returned light acquired in advance with respect to the standard sample.

\* \* \* \* \*